(12) United States Patent
Ugarkovic

(10) Patent No.: US 6,572,891 B1
(45) Date of Patent: Jun. 3, 2003

US006572891B1

(54) SUBLINGUAL ORAL DOSAGE FORM

(75) Inventor: Sonja Jovan Ugarkovic, Skopje (MK)

(73) Assignee: Alkaloid Ad, Skopje (MK)

( * ) Notice: Subject to any disclaimer, the term of this patent is extended or adjusted under 35 U.S.C. 154(b) by 0 days.

(21) Appl. No.: 09/658,205

(22) Filed: Sep. 8, 2000

Related U.S. Application Data

(63) Continuation-in-part of application No. 09/593,410, filed on Jun. 14, 2000, now abandoned, which is a continuation-in-part of application No. 09/489,430, filed on Jan. 21, 2000, now abandoned.

(51) Int. Cl.[7] ............................. A61K 9/14; A61K 31/44
(52) U.S. Cl. ..................... 424/489; 514/282; 229/206
(58) Field of Search ........................ 424/489; 514/282; 229/206

(56) References Cited

U.S. PATENT DOCUMENTS

| | | | |
|---|---|---|---|
| 4,599,342 A | * | 7/1986 | LaHann ........................ 514/28 |
| 5,411,745 A | * | 5/1995 | Oshlack et al. .............. 424/456 |
| 5,767,125 A | | 6/1998 | Crain et al. .................. 514/282 |
| 5,785,989 A | * | 7/1998 | Stanley et al. ............... 424/440 |
| 5,811,126 A | | 9/1998 | Krishnamurthy ............ 424/498 |
| 5,876,754 A | | 3/1999 | Wunderlich et al. ........ 424/489 |
| 6,103,261 A | | 8/2000 | Chasin et al. ................ 424/459 |
| 6,103,269 A | | 8/2000 | Wunderlich et al. ........ 424/489 |

FOREIGN PATENT DOCUMENTS

| | | | |
|---|---|---|---|
| EP | 0 080 047 | 6/1983 | ......... A61K/31/485 |
| WO | WO 94/07761 | 4/1994 | ........... B65D/75/32 |
| WO | WO 99/24023 | 5/1999 | ........... A61K/31/00 |

* cited by examiner

*Primary Examiner*—Michael G. Hartley
*Assistant Examiner*—Robert M DeWitty
(74) *Attorney, Agent, or Firm*—Darby & Darby

(57) ABSTRACT

A pharmaceutical sublingual solid dosage form comprising a morphine salt together with excipients including a saccharide, a binder and a disintegrant. A method of manufacturing the dosage form is also described, together with packaging suitable for long term storage of the dosage form.

17 Claims, No Drawings

SUBLINGUAL ORAL DOSAGE FORM

This is a continuation-in-part application of U.S. Ser. No. 09/593,410 filed Jun. 14, 2000, now abandoned, which is a continuation-in-part application of U.S. Ser. No. 09/489,430 filed Jan. 21, 2000, now abandoned, which is hereby incorporated by reference in its entirety and which claims priority from Great Britain Patent Application No. 9925069.8 filed Oct. 23, 1999.

This invention relates to a pharmaceutical oral dosage, particularly to a formulation for administration of a salt of morphine or a morphine derivative. In particular the present invention is concerned with a formulation containing morphine sulphate.

Morphine is used for control of moderate to severe pain and morphine salts have historically been administered by different routes. Solutions or delay release oral formulations have been used for treatment of chronic pain, for example in cancer patients. However adverse effects include gastrointestinal disturbances, constipation and difficulty in establishing the correct dosage. Metabolism of morphine by the liver makes higher doses necessary. Controlled release formulations are difficult to administer to patients suffering from swallowing disorders. Poor absorption from controlled release buccal tablets has also been reported.

Formulations containing morphine are well documented in the prior art.

U.S. Pat. No. 6,077,533 discloses an oral dosage form of morphine which is formulated by powder layering an homogeneous mixture of morphine sulphate and hydrous lactose impalpable on to inert beads to obtain a multi-particular product. The advantage of this product is that it provides a high-load immediate release multi-particulate formulation of morphine giving effective blood plasma levels for up to 4 hours, which can be formulated for extended release to provide effective blood plasma levels for 12 to 24 hours.

U.S. Pat. No. 6,083,531 discloses a solid dosage form for oral administration consisting of an active substance, a filler, a binding agent and excipients but specifically no agar. The formulation disintegrates in the mouth in 15 seconds without chewing. However, the tablet is not intended for sublingual use and this disclosure does not envisage morphine or other opioids amongst the suitable active ingredients in the formulation.

U.S. Pat. No. 5,580,876 discloses a method of selectively enhancing the analgesic potency of a bimodally-acting opioid such as morphine and simultaneously attenuating the anti-analgesia, hyperalgesia, hyperexcitability, physical dependence and/or tolerance effects associated with the administration of the bimodally-acting opioid agonist. The author suggests in general terms that the formulation may be presented as capsules, tablets, powders, granules or a suspension for oral or sublingual administration. However, there are no examples of suitable sublingual formulations and no disclosure that morphine may be incorporated in such a formulation or indeed how it could be so incorporated.

U.S. Pat. No. 5,411,745 discloses an oral morphine dosage form in which a mixture of morphine sulphate and lactose is coated on to inert beads to provide an immediate release formulation. This disclosure provides of both an immediate and extended duration effect. The formulation is not intended for sublingual delivery and the immediate release beads are loaded into gelatine capsules which are to be swallowed.

Morphine may also be administered by injection. However patients are often averse to receiving repeated injections. Fear of injections may lead children or other patients to endure pain unnecessarily. Injectable dosage forms have also been used for emergency treatment of injuries including by self administration. However self injection kits may be difficult to use correctly dependent on the nature of the user's injury. Furthermore the kit is more bulky than a tablet of equivalent strength so that carriage of single of multiple doses for emergency prophylactic use is less convenient.

One problem of oral morphine dosage forms is due to the bitter taste of morphine. This may interfere with patient compliance. Sublingual absorption may be reduced due to involuntary swallowing by the patient.

There is a need for a need for a formulation containing morphine or a derivative of morphine which can be administered sublingually for the emergency and immediate relief of chronic pain. It is an object of the invention to provide such a formulation. It is a further object to provide a formulation which is convenient to administer, and which can be self administered in emergency situations. One object of the invention is to provide a formulation which is sufficiently palatable for sublingual use and which avoids the tendency of involuntary swallowing by a patient. Another object of the invention is to provide a simple unit-dosage regimen for immediate usage. There is also a need for a formulation which is able to provide a rapid onset of analgesia and the present invention satisfies this need.

According to a second aspect of the present invention there is provided a pharmaceutical sublingual solid dosage form comprising a salt of morphine or a morphine derivative, one or more soluble saccharides as fillers, a binder and a disintegrant.

The morphine salt may be the sulphate, phosphate, hydrochloride, tartrate or less preferably the acetate. Mixtures may be employed.

Various salts of the same active compound often behave quite differently and in ways which are not empirically predictable. This may be due to the different chemical or thermodynamic properties of the active salt compound as a whole. Thus different salts of the same active usually have quite similar physiological effects. However, the intensities of response of a variety of salts may vary widely. In this regard, we have found that the sulphate salt of morphine gives particularly good dissolution and bioavailability. This finding is surprising because the more soluble tartrate salt of morphine is less efficacious. Thus the sulphate salt of morphine is preferred on account of the excellent dissolution of formulations in accordance with this invention both in vitro and in vivo.

The lattice structure of a crystalline molecule can be modified by the presence of a solvent such as water and this may have a profound input on the bulk properties of the active ingredient. Thus the particle size distribution and solubility-related properties will depend upon the hydration state of the active. However, it is not possible to predict the effect of varying the hydration state on these properties. We have found that the pentahydrate of morphine sulphate is particularly advantageous in the sub-lingual formulations of the present invention. A formulation based on the pentahydrate of morphine sulphate in particular shows a remarkable degree of solubility despite the apparent poorer solubility of morphine sulphate compared with other salts of morphine. It is also surprising that a stable solid formulation can be produced from the pentahydrate of morphine sulphate since morphine is known to undergo slow degradation in the presence of air and water vapour. Furthermore the bulk properties facilitate tabletting.

Salts of morphine derivatives which may be employed include salts of diacetyl morphine (diamorphine), and oxycodione, and combinations thereof. The salts may be selected from sulphate, phosphate, hydrochloride, tartrate and acetate. Diamorphine and oxycodone are preferably in the form of hydrochloride salts.

A dosage form in accordance with this invention is preferably rapidly soluble when introduced into the oral cavity. A dissolution time of about two minutes or less is preferred. However morphine salts have an unpleasant bitter taste which makes administration of a soluble dosage form unpleasant and difficult, for example to children. The sweetness of the saccharides reduces the unpalatable taste of the active ingredient. The saccharide or saccharides used are preferably rapidly soluble in saliva.

Tablets in accordance with this invention release 90% of the active ingredient when placed in 500 cm$^3$ of distilled water for 5 min at 37° C. using the apparatus specified in USP23 with a basket run at a speed of 100 rpm.

In a preferred embodiment the release time is 2 min or less. The onset of analgesia may thus be achieved in only 20 to 30 minutes using the formulations of the present invention. In contrast, traditional oral formulations typically give onset of analgesia in 50 or 60 minutes.

In preferred embodiments of the invention the bitter taste is not completely masked. A residual slightly bitter taste is preferred so that the patient is aware that a potent dosage form has been administered. In preferred embodiments the bitter taste is experienced for one to two minutes.

Rapid dissolution of the dosage form which is necessary to facilitate sublingual absorption may be achieved by selection of an appropriate method of tablet manufacture. Use of direct compression or dry granulation has been found to be less suitable than wet granulation, due to the high bulk density and electrostatic properties of morphine salts, for example morphine sulphate, and excipients.

According to another aspect of the present invention, a method of manufacture of a pharmaceutical solid dosage form of a morphine salt comprises the steps of:

mixing a salt of morphine or a morphine derivative with one or more excipients selected from saccharides, disintegrants and binders;

wet granulating the mixture;

milling, drying and sieving the resultant granules;

adding a lubricant; and compressing the resultant granulate into tablets.

In another aspect of the present invention, there is provided a method of treating chronic pain by administering a therapeutically effective dosage of a salt of morphine or a morphine derivative in the form of a sublingual tablet.

In a further aspect of the invention, there is provided a blister pack including a plurality of blister pockets wherein each individually openable blister pocket includes a sublingual dosage form containing a salt of morphine or a morphine derivative in unit dosage form, and wherein the blister pack is substantially impervious to air and moisture.

The blister pack preferably enables storage of the sublingual formulation for at least two years without degradation of the formulation due to the ingress of air or water vapour. Optionally, the blister pack may be impervious to light also. The blister pack is thus suitable for long term storage of the dosage form for immediate "in-the-field" use.

In a preferred method all of the saccharide or mixture saccharides is granulated together with the morphine salt or derivative and a proportion of the disintegrant, the dried, sieved granulate being combined with the remainder of the disintegrant and lubricant and compressed into tablets. This method provides better homogeneity of granulate than if a proportion of the saccharide is added after granulation.

Granulation may be carried out using water or an aqueous solvent mixture. Preferably, the average particle size is not more than 0.3 mm to facilitate tableting into a stable formulation. The mesh size used in the granulation step should preferably be less than 0.70 mm in order to obtain the advantageous particle size distribution.

Tablets of the present invention preferably comprise compacted granulates together with an extra-granular disintegrant and a minimal quantity of an extra-granular lubricant.

Tablets in accordance with this invention which provide convenient dosages may include morphine sulphate in an amount of 10 mg, 20 mg or 30 mg. The quantity of active substance may vary in the gross weight of the tablet although the relative proportions of excipients may be as described below. A minimum quantity of excipients is preferred in order to enhance complete sublingual absorption.

Further, a minimum number of excipients is preferred in order to enhance the sublingual absorption. Thus a preferred formulation includes only the salt of morphine or the morphine derivative, the filler (preferably mannitol, lactose, xylitol and mixtures thereof), the binder (preferably gelatin), and the disintegrant.

Rapid sublingual absorption is preferred in order to give a quick pain killing effect. This is particularly important for treatment of a patient after an injury or if quick treatment of chronic pain is necessary. The sublingual formulation of the invention is particularly suitable for administration to patients with swallowing difficulties or for paediatric use. Patients may have difficulty in swallowing because of a throat disorder or injury and the presently claimed formulation is particularly beneficial in these cases. Patients may also not have a large quantity of saliva so that a larger tablet may not be completely and rapidly dissolved if at all. Passage of an undissolved dosage form from the mouth into the throat is thus undesirable and is avoided using the formulations of the invention. It is therefore to minimise the size of the dosage form and dosage forms in accordance with this invention preferably have a minimum size, eg 6 mm diameter and corresponding weight whilst maintaining the dosage of 10, 20 or 30 mg. Preferably the total tablet weight does not exceed 100 mg, and more preferably it is less than 70 mg.

A dosage form in accordance with this invention has the advantage that a minimum quantity of morphine or derivative thereof may be administered in a dose-to-effect manner. The onset of pain relief is rapid so that one or more tablets may be administered sublingually successively until pain relief is achieved. Thereafter further doses may be administered in the quantities necessary to maintain analgesia and the tablets may be given without continuing medical supervision.

In contrast, sustained release dosage forms are less rapidly absorbed and consequently may be given in a higher dose in order to achieve rapid onset of pain relief. There is a higher risk of initial overdosage with sustained release formulations so that more stringent medical supervision may be required. Administration of a high dosage of morphine increases the likelihood of development of tolerance and habituation of a patient.

Dosage forms in accordance with the present invention also have the advantage that they may be administered in a domestic environment without close medical supervision.

A dosage form in accordance with the invention also reduces the possibility of deliberate or inadvertent deception of a physician or nurse by a patient who wishes to receive a higher dose than necessary since the onset of pain relief is very rapid with the formulations of the invention.

Repeated doses of morphine are usually necessary, particularly for treatment of chronic pain. An optimum dosage form delivers a minimum quantity of morphine but in the highest effective dose. Sustained release dosage forms require higher quantities of morphine to overcome the first pass effect whereby morphine is metabolised on passage through the liver. There is thus also the benefit that the formulations of the present invention actually enable a lower dosage to be administered to the patient. Indeed, the dosage levels and onset times are, surprisingly, similar to those of IV dosage levels.

Suitable disintegrants include starches such as maize starch and rice starch, cross-linked N-vinyl-2-pyrrolidone (CLPVP), sodium starch glycolate, croscarmelose sodium and formaldehyde casein or combinations thereof. A preferred disintegrant is sodium starch glycolate. The disintegrant may be present as an intra-granular disintegrant or extra-granular disintegrant.

The proportion of the disintegrant may be 0.1 to 10% of the granule, preferably 1 to 4%, more preferably 1.5 to 3%.

A binder may be employed, in a minimum quantity to prevent unnecessary reduction in the rate of dissolution. A preferred binder is gelatin although polyvinyl pyrolidone or hydroxymethyl polyvinyl pyrolidone may also be used. Preferred binders are soluble in water. Gelatin has been found to bind tablets of good quality which disintegrate within two minutes. If the amount of gelatin exceeds 1.8%, preferably 1.5% by weight of release of the morphine or morphine derivative is reduced. Likewise, if there is less than 0.6%, preferably 0.8% by weight of gelatin the binding of the formulation deteriorates. An amount of 0.8 to 1.5% of gelatin is thus especially preferred.

Suitable lubricants include magnesium or calcium stearates or other long chain fatty acid salts. Magnesium stearate is especially preferred. A minimal proportion of lubricant is preferred, for example up to 1%, preferably about 0.8%. The lubricant may be an intra-granular lubricant, extra-granular lubricant or both. Use of an extra-granular lubricant alone is preferred in order to minimise the hydrophobic properties of the dosage form.

The tablet may also include conventional excipients typically present at up to about 10% of the total weight. These may include flavouring agents, for example flavourings such as menthol, peppermint, vanilla or fruit flavourings. Flavouring agents when used are typically present up to about 0.5 to 5% by weight of the whole tablet. Sweeteners eg aspartame or sodium saccharinate may be used. Further excipients may also include colouring agents, preservatives and fillers.

Preferred fillers are selected from saccharides. Mannitol, lactose, xylitol and mixtures thereof are preferred on account of their solubility and despite the water content of lactose in particular. Mannitol may be present in an amount of 20 to 40% for example 20 to 30% by weight. Lactose may be present in an amount of 30 to 60%, preferably 45 to 60% by weight.

The blister pack in which the formulations may be used for long term storage may in one embodiment be a multi-layered foil laminate having at least one layer of plastics, preferably as an interior layer, and at least one layer of metallic foil. The laminated structure thus at least comprises: a metallic foil layer and a layer of a plastics film which may itself be a single layer or a laminate. Preferably the blister pockets within which the sublingual tablets are individually located are formed in the plastic layer. These pockets may be formed by injection moulding. The plastics layer and/or the metallic layer may have indicia imprinted on a surface thereof. In another arrangement, the blister pack may be in the form of a sandwich structure with metallic foil being laminated to both sides of the plastics thereof. In further arrangement, the blister pack may be in the form of a metallic foil having a plastics liner. Two laminated sheets of plastics and metallic foil thus form the pack, with the two plastics layers being adjacent on the inside of the pack and forming the blister or bubble in which the tablets are individually stored. The metallic foil layers represent the exterior layers.

The plastics layer may be translucent and may be formed of polyester or other plastics material having suitable gas barrier properties. Laminated plastics films, for example containing one or more of PVC, PVdC, EVOH, EVA, polypropylene, LLDPE, and LDPE and the like, may be used provided the gas barrier properties of the material do not allow the transmission of air or water vapour. PVC and TE (thermoplastic) PVdC are preferred. Where the plastics is laminated a laminate of PVC and PVdC is preferred.

Preferably the metallic foil consists of aluminium with polyvinyl chloride (PVC)/thermoelastomer PvdC.

A blister pack composed of aluminium foil and PVC/thermoplastic PVdC foil provides an excellent barrier to external contaminants and air. This feature contributes to the long term storage of the formulations.

The blister pack thus enable storage of the sublingual tablets for an extended period without any significant deterioration of the tablets due to exposure to air or water. The tablets may thus be stored for at least 2 years, and preferably more than 3 years, without losing any therapeutic effectiveness.

The invention is further described by means of examples but not in any limitative sense.

Amounts and percentages used in this specification are by weight unless indicated otherwise. Percentages are selected to total 100%.

EXAMPLE 1

| | |
|---|---|
| Morphine sulphate | 10.000 mg |
| Mannitol | 19.000 mg |
| Sodium starch glycolate (Primojel(trade mark)) | 1.200 mg |
| Lactose (Pharmatose (trade mark)) 100 M | 38.282 mg |
| Magnesium stearate | 0.600 mg |
| Gelatin | 0.918 mg |
| | 70.000 mg |

A binding solution was prepared by addition of gelatin to cold purified water followed by heating on a water bath to a temperature of about 75° C. until a clear solution was obtained. Morphine sulphate, mannitol and half of the sodium starch glycolate was mixed. The homogeneous mixture was wet granulated with the binder solution. The granulates were wet sieved, dried and ground using a screen of mesh size 0.63 nm. The resultant dry granules were mixed with lactose monohydrate and the second half of the sodium starch glycolate. The lubricant was added and the final mixture was compressed to form tablets having a weight of 70 mg.

A high performance liquid chromatographic procedure was used for the quantification of morphine sulphate. A Varian Modular H Plc system was used. This consisted of a 9010 solvent delivery system, a 9050 variable wavelength UV-VIS detector operated at 290 nm, and a 9300 auto sample equipped with a 20 μl sample loop. Chromatograms were collected and integrated using a 4400 integrator. The separation was performed on a LiChrospher 100 RP-18 (25×4 mm id; 5 µm) column. The mobile phase was buffer (pH 7):methanol:acetronitrile (50:10:40) at a flow rate of 1 ml/min. 20 µl injections were used. The chromatography was carried out at room temperature. The eluent was monitored at 290 nm.

A standard solution was prepared by dissolving morphine sulphate RS in the mobile phase to obtain a concentration of 0.2 mg/ml.

Not less than twenty tablets were weighed and finely powdered. An amount of powder equivalent to one tablet was accurately weighed, dissolved and diluted to 50 ml with the mobile phase.

The standard and sample solutions were filtered through a 0.45 µm membrane filter and 20 µl of each sample was injected into HPLC system.

Results

Assay: 10.45 mg morphine sulphate/ling, per tablet or 104.58% of the declared amount (92.5–107.5%)

Content uniformity:

max 112.43% min 94.62% (85–115%)

Relative Standard Deviation: 4.02% (max 6%)

Dissolution Test

Equipment: USP 23 (with basket)

Dissolution medium: 500 ml distilled water

Temperature: 37° C.

Speed: 100 rpm

Time: 5 min

Procedure

When the system was thermostatic at 37° C. One tablet was added to each dissolution vessel. After 5 min an aliquot of 10 ml was taken from each vessel and filtered through a 0.45 µm membrane filter, discarding the first ml.

Standard Preparation

Exactly 20 mg of morphine sulphate RS (relative standard) was weighed and transferred quantitatively to a 100 ml volumetric flask. The sample was filtered through 0.45 µm membrane filter, discharging the first ml. The equipment and chromatographic parameters as described above were used except that the detection was at 285 nm.

Results

After 2 min: 94.38% of declared amount

After 5 min: 103.51% of declared amount

Tablets with final composition packaged in amber glass bottles with a screw cap demonstrated a good physical and chemical stability during two years period.

EXAMPLE 2

| Morphine Sulphate | 20.000 mg |
| --- | --- |
| Mannitol | 15.000 mg |
| Sodium Starch Glycolate | 1.800 mg |
| Lactose | 31.600 mg |
| Magnesium Stearate | 0.600 mg |
| Gelatine | 1.00 mg |
| | 70.000 mg |

A premixture of morphine sulphate, mannitol, sodium starch glycolate and lactose was granulated using a binder as in Example 1. The granules were wet screened, dried and ground to the required size by use of a screen having a mesh size of 0.63 mm. The produced granules were mixed with the lubricant, and the final mixture was compressed into tablets having a mass of 70 mg.

EXAMPLE 3

| Morphine Sulphate | 20.000 mg |
| --- | --- |
| Mannitol | 27.140 mg |
| Sodium Starch Glycolate | 1.750 mg |
| Lactose | 49.210 mg |
| Magnesium Stearate | 0.800 mg |
| Gelatine | 1.310 mg |
| | 100.000 mg |

A premixture of morphine sulphate, mannitol, lactose and two thirds of the disintegrant sodium starch glycolate was granulated using a binder using the method of Example 1. The granules were wet screened, dried and ground to the required size by use of a screen having a mesh size of 0.63 mm. The granules produced were mixed with the lubricant and with one third of the disintegrant.

EXAMPLE 4

| Morphine Sulphate | 30.000 mg |
| --- | --- |
| Mannitol | 25.000 mg |
| Sodium Starch Glycolate | 1.750 mg |
| Lactose | 41.140 mg |
| Magnesium Stearate | 0.800 mg |
| Gelatin | 1.310 mg |
| | 100.000 mg |

The production procedure of Example 3 was used.

The composition of the sublingual tablets of the previous examples may be modified by addition of either aspartame or sodium saccharinate as a sweetener in an amount of 0.01% and a flavour, eg grapefruit, in an amount of 0.5% as the most appropriate combination to disguise the bitter taste of the morphine sulphate.

EXAMPLE 5

| Morphine Sulphate | 20.00 mg |
| --- | --- |
| Mannitol | 20.00 mg |
| Xylitol | 27.00 mg |
| Magnesium stearate | 0.60 mg |
| Gelatin | 0.60 mg |
| Sodium Starch Glycolate | 1.80 mg |
| | 70.00 mg |

The production procedure of Example 3 was used.

What is claimed is:

1. A pharmaceutical sublingual solid dosage form comprising:
   (a) a therapeutically effective amount of an active ingredient consisting essentially of a salt of morphine, diamorphine or oxycodone or a mixture thereof;
   (b) one or more saccharides as fillers;
   (c) from 0.6 to 1.8% by weight of gelatin; and (d) from 0.1 to 10% by weight of a disintegrant;

said solid dosage form releasing 90% of said salt when placed in 500 cm³ of distilled water for 5 minutes at 37° C. using the apparatus specified in USP23 with a basket run at a speed of 100 rpm.

2. A dosage form as claimed in claim 1, wherein the morphine salt is morphine sulphate pentahydrate.

3. A dosage form as claimed in claim 1, wherein the salt of diamorphine is diamorphine hydrochloride.

4. A dosage form as claimed in claim 1, wherein the filler comprises a soluble saccharide selected from the group consisting of mannitol, lactose, xylitol and mixtures thereof.

5. A dosage form as claimed in claim 4, comprising 20 to 40% by weight of mannitol and 30 to 60% by weight of lactose.

6. A dosage form as claimed in claim 1, wherein the amount of gelatin is 0.8 to 1.5% by weight.

7. A dosage form as claimed in claim 1, comprising granulates compacted by wet granulation.

8. A method of treating chronic pain by administering a therapeutically effective amount of an active ingredient consisting essentially of a salt of morphine, diamorphine or oxycodone or a mixture thereof in the form of a sublingual tablet, said sublingual tablet additionally comprising:

(a) from 0.6 to 1.8% by weight of gelatin; and (b) from 0.1 to 10% by weight of a disintegrant;

said sublingual tablet releasing 90% of said salt when placed in 500 cm³ of distilled water for 5 minutes at 37° C. using the apparatus specified in USP23 with a basket run at a speed of 100 rpm.

9. A method for administering morphine to a patient in need thereof comprising the step of sublingually administering a dosage form to the patient, the dosage form comprising:

(a) a therapeutically effective amount of an active ingredient consisting essentially of morphine sulphate pentahydrate;

(b) a filler comprising at least one saccharide;

(c) from 0.6 to 1.8% by weight of gelatin; and (d) from 0.1 to 10% by weight of a disintegrant;

said solid dosage form releasing 90% of said morphine sulphate pentahydrate when placed in 500 cm³ of distilled water for 5 minutes at 37° C. using the apparatus specified in USP23 with a basket run at a speed of 100 rpm.

10. The method of claim 9, wherein the filler comprises a saccharide selected from the group consisting of mannitol, lactose, xylitol, and mixtures thereof.

11. The method of claim 10, wherein the dosage form comprises 20 to 40% by weight of mannitol and 30 to 60% by weight of lactose, based upon 100% total weight of dosage form.

12. The method of claim 9, wherein the dosage form comprises granulates of morphine sulphate pentahydrate compacted by wet granulation.

13. The method of claim 9, wherein at least 90% of the morphine sulphate pentahydrate is released in 2 minutes or less.

14. A pharmaceutical sublingual solid dosage form comprising:

(a) a therapeutically effective amount of an active ingredient consisting essentially of a salt of morphine, diamorphine or oxycodone or a mixture thereof;

(b) from 20 to 40% by weight of mannitol;

(c) from 30 to 60% by weight of lactose;

(d) from 0.6 to 1.8% by weight of gelatin; and (e) from 0.1 to 10% by weight of a disintegrant;

said solid dosage form releasing 90% of said salt when placed in 500 cm³ of distilled water for 5 minutes at 37° C. using the apparatus specified in USP23 with a basket run at a speed of 100 rpm.

15. The pharmaceutical sublingual solid dosage form according to claim 14 wherein the salt of morphine is morphine sulphate pentahydrate.

16. The pharmaceutical sublingual solid dosage form according to claim 15, wherein at least 90% of the morphine sulphate pentahydrate is released in 2 minutes or less.

17. A dosage form as claimed in claim 1 wherein the salt of oxycodone is oxycodone hydrochloride.

* * * * *

UNITED STATES PATENT AND TRADEMARK OFFICE
CERTIFICATE OF CORRECTION

PATENT NO. : 6,572,891 B1  Page 1 of 1
DATED : June 3, 2003
INVENTOR(S) : Sonja Ugarkovic It is certified that error appears in the above-identified patent and that said Letters Patent is hereby corrected as shown below:

<u>Title page,</u>
Insert Item

-- [30]   Foreign Application Priority Data

October 23, 1999  (UK) …………………..9925069.8 --

Signed and Sealed this

Eighteenth Day of November, 2003

JAMES E. ROGAN
*Director of the United States Patent and Trademark Office*